(12) United States Patent
Humphries et al.

(10) Patent No.: US 9,493,613 B2
(45) Date of Patent: Nov. 15, 2016

(54) ORGANIC LIGHT EMITTING COMPOSITION, DEVICE AND METHOD

(75) Inventors: Martin Humphries, Cambridgeshire (GB); Richard J. Wilson, Cambridgeshire (GB)

(73) Assignees: Cambridge Display Technology, Ltd., Godmanchester (GB); Sumitomo Chemical Company Limited, Tokyo (JP)

(*) Notice: Subject to any disclaimer, the term of this patent is extended or adjusted under 35 U.S.C. 154(b) by 214 days.

(21) Appl. No.: 14/130,922

(22) PCT Filed: Jul. 3, 2012

(86) PCT No.: PCT/GB2012/051555
§ 371 (c)(1),
(2), (4) Date: Apr. 3, 2014

(87) PCT Pub. No.: WO2013/005029
PCT Pub. Date: Jan. 10, 2013

(65) Prior Publication Data
US 2014/0217379 A1    Aug. 7, 2014

(30) Foreign Application Priority Data

Jul. 4, 2011 (GB) .................................... 1111360.2
Jul. 4, 2011 (GB) .................................... 1111372.7
(Continued)

(51) Int. Cl.
*H01L 51/00* (2006.01)
*C08G 73/02* (2006.01)
(Continued)

(52) U.S. Cl.
CPC ............ *C08G 73/026* (2013.01); *C08G 61/12* (2013.01); *C08L 65/00* (2013.01);
(Continued)

(58) Field of Classification Search
None
See application file for complete search history.

(56) References Cited

U.S. PATENT DOCUMENTS 4,540,763 A    9/1985    Kirchhoff
4,567,181 A    1/1986    Malen et al.
(Continued)

FOREIGN PATENT DOCUMENTS

EP    0402975 A2    12/1990
EP    2308910 A1    4/2011
(Continued)

OTHER PUBLICATIONS

International Search Report and Written Opinion for International Application No. PCT/GB2012/051555 dated Nov. 14, 2012.
(Continued)

*Primary Examiner* — Vu A Nguyen
(74) *Attorney, Agent, or Firm* — Wolf, Greenfield & Sacks, P.C.

(57) ABSTRACT

Disclosed is a crosslinkable light-emitting composition comprising at least one host material, at least one phosphorescent light-emitting dopant, a first crosslinker comprising an unsaturated carbon-carbon bond group and a second crosslinker comprising a ring system capable of undergoing ring-opening crosslinking.

19 Claims, 1 Drawing Sheet

(30) Foreign Application Priority Data

Jul. 4, 2011 (GB) .................................. 1111375.0
Nov. 22, 2011 (GB) .................................. 1120131.6

(51) Int. Cl.
C08G 61/12 (2006.01)
C08L 65/00 (2006.01)
H01L 51/50 (2006.01)

(52) U.S. Cl.
CPC ....... *H01L 51/0007* (2013.01); *H01L 51/0043* (2013.01); *H01L 51/5016* (2013.01); *H01L 51/5044* (2013.01); *C08G 2261/12* (2013.01); *C08G 2261/135* (2013.01); *C08G 2261/141* (2013.01); *C08G 2261/1414* (2013.01); *C08G 2261/1434* (2013.01); *C08G 2261/312* (2013.01); *C08G 2261/3142* (2013.01); *C08G 2261/3221* (2013.01); *C08G 2261/374* (2013.01); *H01L 51/0039* (2013.01); *H01L 51/0085* (2013.01); *H01L 51/5004* (2013.01)

(56) References Cited

U.S. PATENT DOCUMENTS

| | | |
|---|---|---|
| 4,638,078 A | 1/1987 | Kirchhoff |
| 4,642,329 A | 2/1987 | Kirchhoff et al. |
| 4,831,172 A | 5/1989 | Hahn et al. |
| 5,387,725 A | 2/1995 | Walters et al. |
| 5,585,450 A | 12/1996 | Oaks et al. |
| 7,893,160 B2 | 2/2011 | Inbasekaran et al. |
| 2002/0076535 A1 | 6/2002 | Cooray |
| 2007/0096082 A1 | 5/2007 | Gaynor et al. |
| 2007/0099026 A1 | 5/2007 | Lee et al. |
| 2007/0228938 A1 | 10/2007 | Hatwar et al. |
| 2008/0169756 A1* | 7/2008 | Son .................. C08G 61/02 313/504 |
| 2009/0045739 A1 | 2/2009 | Kho et al. |
| 2009/0226757 A1 | 9/2009 | Song et al. |
| 2010/0062643 A1 | 3/2010 | Kumagai et al. |
| 2010/0090238 A1 | 4/2010 | Mori et al. |
| 2010/0163854 A1 | 7/2010 | Kho et al. |
| 2010/0270539 A1 | 10/2010 | Nishimura et al. |
| 2012/0306358 A1* | 12/2012 | Hirano ............... C08G 61/12 313/504 |

FOREIGN PATENT DOCUMENTS

| | | |
|---|---|---|
| EP | 2518111 A1 | 10/2012 |
| EP | 2520576 A1 | 11/2012 |
| JP | 2003-285570 | 10/2003 |
| JP | 2003-287882 | 10/2003 |
| WO | WO 86/01503 A1 | 3/1986 |
| WO | WO 2005/049689 A2 | 6/2005 |
| WO | WO 2008/024435 A2 | 2/2008 |
| WO | WO 2008/025997 A1 | 3/2008 |
| WO | WO 2010/115498 A1 | 10/2010 |
| WO | WO 2011/078391 A1 | 6/2011 |

OTHER PUBLICATIONS

International Search Report and Written Opinion for International Application No. PCT/GB2012/051552 dated Jan. 30, 2013.
Combined Search and Examination Report for Application No. GB1120131.6 dated Mar. 22, 2012.
Combined Search and Examination Report for Application No. GB1111360.2 dated Oct. 31, 2011.
Combined Search and Examination Report for Application No. GB1111372.7 dated Nov. 9, 2011.
Combined Search and Examination Report for Application No. GB1111375.0 dated Mar. 5, 2012.

* cited by examiner

ORGANIC LIGHT EMITTING COMPOSITION, DEVICE AND METHOD

RELATED APPLICATIONS

The present application is a national stage filing under 35 U.S.C. §371 of international PCT application, PCT/GB2012/051555, filed Jul. 3, 2012, which claims priority to United Kingdom patent application, GB 1120131.6, filed Nov. 22, 2011, United Kingdom patent application, GB 1111375.0, filed Jul. 4, 2011, United Kingdom patent application, GB 1111372.7, filed Jul. 4, 2011 and United Kingdom patent application, GB 1111360.2, filed Jul. 4, 2011, each of which is incorporated herein by reference.

SUMMARY OF THE INVENTION

The present invention relates to organic light-emitting compositions, organic light-emitting devices and methods of making the same.

BACKGROUND

Electronic devices comprising active organic materials are attracting increasing attention for use in devices such as organic light emitting diodes (OLEDs), organic photoresponsive devices (in particular organic photovoltaic devices and organic photosensors), organic transistors and memory array devices. Devices comprising organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode. One or more organic charge transporting and/or one or more charge blocking layers may also be provided between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Suitable light-emitting materials include small molecule, polymeric and dendrimeric materials. Suitable light-emitting polymers include poly(arylene vinylenes) such as poly(p-phenylene vinylenes) and polyarylenes such as polyfluorenes.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton) and Appl. Phys. Lett., 2000, 77, 904 discloses a host material doped with a phosphorescent light emitting dopant (that is, a light-emitting material in which light is emitted via decay of a triplet exciton).

Formation of the one or more organic layers of an OLED may be by deposition of materials used to form those layers from a solution in a solvent followed by evaporation of the solvent. Examples of suitable solution processing methods include coating methods such as spin-coating or dip-coating and printing methods such as inkjet printing or roll-to-roll printing.

In devices comprising multiple organic layers, a first deposited organic layer may be rendered insoluble by crosslinking prior to deposition of a further organic layer by a solution processing method in order to prevent dissolution of the first deposited layer by the solvent used in formation by solution processing of the further organic layer. WO 2005/049689 discloses polymers comprising fluorene repeat units substituted with crosslinkable groups, including a double bond, a triple bond, a precursor capable of in situ formation of a double bond or a heterocyclic, addition polymerisable group. Benzocyclobutane (BCB) is disclosed as an exemplary crosslinkable group.

WO 2010/013723 discloses polymers comprising double bond groups and BCB groups.

Emission from more than one layer of an OLED, in particular to achieve white light emission, is disclosed in, for example, WO 2008/131750, DE 102007020644 and EP1390962 and SPIE (2004), 5519, 42-47.

SUMMARY OF THE INVENTION

In a first aspect the invention provides a crosslinkable light-emitting composition comprising at least one host material, at least one phosphorescent light-emitting dopant, a first crosslinker comprising an unsaturated carbon-carbon bond group and a second crosslinker comprising a ring system capable of undergoing ring-opening crosslinking.

Optionally, the at least one light-emitting dopant is blended with the host material.

Optionally, the at least one light-emitting dopant is bound to the host material.

Optionally, the first crosslinker comprises a carbon-carbon double bond, preferably a terminal double bond.

Optionally, the ring system comprises cyclobutane.

Optionally, the ring system comprises an optionally substituted polycyclic ring system.

Optionally, the polycyclic ring system comprises an optionally substituted benzocyclobutane group.

Optionally, at least one of the first and second crosslinkers is a crosslinking compound mixed in the composition.

Optionally, the at least one host material is a polymer.

Optionally, the phosphorescent light-emitting dopant is a repeat unit in the polymer main chain, a side group of the polymer or an end-group of the polymer.

Optionally, at least one of the first and second crosslinker is a substituent of the at least one host material.

Optionally, at least one of the first and second crosslinker is provided in a side group or end group of the polymer.

Optionally, the second crosslinker is capable of forming a diene, the diene being capable of reacting with the unsaturated carbon-carbon bond group of the first crosslinker.

In a second aspect the invention provides a formulation comprising a crosslinkable light-emitting composition according to the first aspect and at least one solvent.

In a third aspect the invention provides a method of forming an organic light-emitting device comprising the steps of:

forming a first organic light-emitting layer by depositing a crosslinkable light-emitting composition according to any preceding claim over a first electrode for injection of charge carriers of a first type and crosslinking the crosslinkable groups; and forming a second electrode for injection of charge carriers of a second type over the first organic light-emitting layer.

Optionally according to the third aspect, the crosslinkable light-emitting composition is a formulation according to the second aspect.

Optionally according to the third aspect, an organic layer is deposited onto the first organic light-emitting layer from a solution in a solvent.

Optionally according to the third aspect, the organic layer is selected from a second light-emitting layer; a charge transporting layer; a charge blocking layer; and an exciton blocking layer.

In a fourth aspect the invention provides an organic light-emitting device comprising a crosslinked light-emitting layer formed from a crosslinkable light-emitting composition according to the first aspect.

Optionally according to the fourth aspect, the device is a white organic light-emitting device.

Optionally according to the fourth aspect, the device comprises at least one further light-emitting layer in addition to the crosslinked light-emitting layer.

DESCRIPTION OF THE DRAWINGS

The invention will now be described in more detail with reference to the drawings, in which.

DETAILED DESCRIPTION OF THE INVENTION

Figure 1:
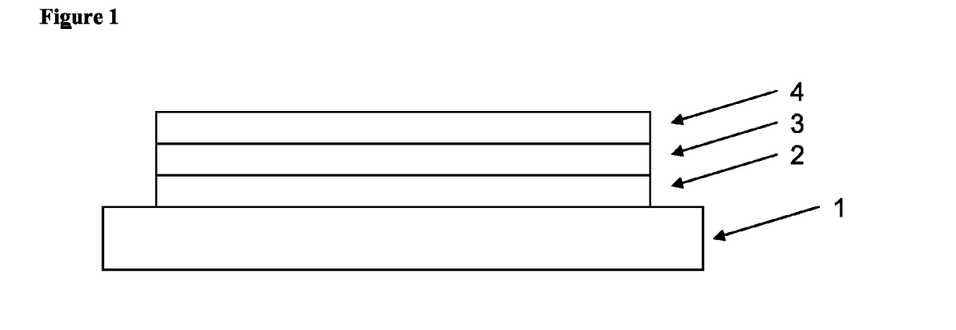
FIG. 1 illustrates schematically an OLED according to an embodiment of the invention.

FIG. 1, which is not drawn to any scale, illustrates schematically an OLED according to an embodiment of the invention. The OLED is carried on substrate 1 and comprises an anode 2, a cathode 4 and a light-emitting layer 3 between the anode and the cathode.

The OLED may be provided with one or more additional layers (not shown) between the anode and the cathode, including one or more further light-emitting layers and/or one or more charge transporting layers, charge blocking layers and/or exciton blocking layers. A plurality of light-emitting layers, in particular two or three light-emitting layers, may be provided to form an OLED that emits white light.

At least one of the light-emitting layers contains a crosslinked host material and a phosphorescent light-emitting dopant, each of which are described in more detail below. Each host material has a triplet energy level $T_1$ that is higher than that of the phosphorescent light-emitting dopant, such that triplet excitons may be transferred from the host material(s) to the dopant.

After the crosslinkable light-emitting layer 3 has been crosslinked, one or more further layers (not shown) may be deposited over the crosslinked layer, and the layer formed on the crosslinked layer may be deposited from a solution in a solvent without causing any significant dissolution of the crosslinked layer.

During formation of the OLED, solution deposition of a layer onto an underlying layer is preferably preceded by crosslinking of the underlying layer, and at least one of the light-emitting layers is crosslinked using the crosslinkers described above. Accordingly, in addition to crosslinking of light-emitting layer 3 using the crosslinkers described above, one or more further organic layers of the OLED that may be present may also be crosslinked using a crosslinking arrangement that is the same as or different to the crosslinker arrangement described above.

Crosslinkers

The composition from which the light-emitting layer 3 is formed contains crosslinkable groups, one of which contains an unsaturated carbon-carbon bond group and the other of which contains a ring system capable of undergoing ring-opening crosslinking.

The crosslinkable groups may be bound to or mixed with the host material or materials. In the case where a host material is a polymer, the crosslinkable groups may be provided as substituents pendant from the polymer backbone or attached to one or more end-groups of the polymer.

Examples of groups capable of undergoing ring-opening crosslinking include the following:

wherein Ar is an optionally substituted aryl or heteroaryl group and * represents a linking position for linking the crosslinkable group to the host material or another carrier material. The crosslinkable material may be bound to the host material and/or to another carrier material, for example a non-conducting polymer with crosslinkable groups. Specific examples include benzocyclobutane:

Examples of crosslinkable groups containing an unsaturated carbon-carbon bond have the following formula:

wherein $R^7$ is H or a substituent and z is 0 or 1. Exemplary substituents $R^7$ include $C_{1-20}$ alkyl and optionally substituted aryl or heteroaryl, for example phenyl substituted with one or more $C_{1-20}$ alkyl groups.

The cyclobutane ring of benzocyclobutane may ring-open to form a diene that is capable of reacting with a dienophile in a Diels-Alder reaction, and any material capable of ring-opening to form a diene suitable for reaction with a dienophile may be used.

Each of the crosslinking groups may independently be substituted with one or more substituents, for example one or more $C_{1-20}$ alkyl groups.

The crosslinking groups may be bound directly to the host material or other carrier, or spaced from the host material or other carrier by a spacer group.

Exemplary spacer groups may form a chain including one or more of groups of formula —$(Ar^7)_p$— and —$(CH_2)_m$— wherein each $Ar^7$ independently represents an optionally substituted aryl or heteroaryl group, for example phenyl optionally substituted with one or more $C_{1-20}$ alkyl groups, p is at least 1, for example 1, 2 or 3; m is at least 1, for example an integer between 1-10; each H of —$(CH_2)_m$— may independently be replaced with a substituent, for example F or an alkyl group, and one or more carbon atoms of —$(CH_2)_m$— may be replaced with a heteroatom, for example O or S.

The crosslinking groups may be crosslinked by, for example, thermal treatment and/or exposure to light (e.g. UV light) having a wavelength and intensity for crosslinking. Crosslinking by thermal treatment may be at a temperature in the range of 100° C.-250° C., optionally 120° C.-200° C. The treatment time may be at least 1 minute, and may be up to about 3 hours, optionally in the range 10 minutes to 2 hours.

Host Materials

The host may be any material having an excited state energy level that is higher than that of the dopant or dopants it is used with, specifically a higher triplet excited state energy level. Preferably, the gap between the host and dopant excited state energy levels is at least kT in order to avoid back transfer of excitons from the dopant to the host material. The host material is optionally solution processable.

Host materials may be selected from small molecule, dendrimeric and polymeric materials having a suitable energy level. Host materials may also be selected according to their highest occupied molecular orbital (HOMO) and/or lowest unoccupied molecular orbital (LUMO) levels to provide little or no bather to hole and electron transport respectively from adjacent layers into the light-emitting layer containing the host material.

The host material may carry one or more of the unsaturated crosslinker and ring-opening crosslinker described above.

Examples of host materials include:
(i) Triazines, for example diaryltriazines or triaryltriazines. Triazine-containing host materials are described in more detail in WO 2008/025997 and include, for example, optionally substituted triphenyltriazine. Optional substituents of the phenyl groups include one or more alkyl groups, for example $C_{1-20}$ alkyl groups. The host may be a small molecule or a polymer comprising triazine repeat units, in particular an optionally substituted di- or triaryltriazine repeat unit attached as a side group through one of the aryl groups, or a repeat unit attached in the polymer main chain through two of the aryl groups. A host polymer comprising triazine repeat units may comprise further repeat units selected from (hetero)arylene co-repeat units, such as phenyl, fluorene or indenofluorene repeat units wherein each of said (hetero)arylene repeat units may optionally be substituted with one or more substituents such as alkyl or alkoxy groups, for example fluorene repeat units as described in more detail below.
(ii) Polymers containing (hetero)arylamine repeat units, either as homopolymers or with one or more co-repeat units such as (hetero)arylene repeat units described below. Exemplary (hetero)arylamine repeat units include repeat units of formula (V):

(V)

wherein $Ar^1$ and $Ar^2$ in each occurrence are independently selected from optionally substituted aryl or heteroaryl groups, n is greater than or equal to 1, preferably 1 or 2, R is H or a substituent, preferably a substituent, and x and y are each independently 1, 2 or 3.

R is preferably alkyl, for example $C_{1-20}$ alkyl, $Ar^3$, or a branched or linear chain of $Ar^3$ groups, for example —$(Ar^3)_r$—, wherein $Ar^3$ in each occurrence is independently selected from aryl or heteroaryl and r is at least 1, optionally 1, 2 or 3.

Any of $Ar^1$, $Ar^2$ and $Ar^3$ may independently be substituted with one or more substituents. Preferred substituents are selected from the group $R^3$ consisting of:
  alkyl, for example $C_{1-20}$ alkyl, wherein one or more non-adjacent C atoms may be replaced with O, S, substituted N, C=O and —COO— and one or more H atoms of the alkyl group may be replaced with F or aryl or heteroaryl optionally substituted with one or more groups $R^4$,
  aryl or heteroaryl optionally substituted with one or more groups $R^4$,
  $NR^5_2$, $OR^5$, $SR^5$,
  fluorine, nitro and cyano;
wherein each $R^4$ is independently alkyl, for example $C_{1-20}$ alkyl, in which one or more non-adjacent C atoms may be replaced with O, S, substituted N, C=O and —COO— and one or more H atoms of the alkyl group may be replaced with F, and each $R^5$ is independently selected from the group consisting of alkyl and aryl or heteroaryl optionally substituted with one or more alkyl groups.

R may comprise a crosslinkable-group, for example an unsaturated or ring-opening crosslinking group as described above that may be either directly bound to the N atom of the repeat unit of formula (V) or spaced from the N atom by a spacer group as described above.

Any of the aryl or heteroaryl groups in the repeat unit of Formula (V) may be linked by a direct bond or a divalent linking atom or group. Preferred divalent linking atoms and groups include O, S; substituted N; and substituted C.

Where present, substituted N or substituted C of $R^3$, $R^4$ or of the divalent linking group may independently in each occurrence be $NR^6$ or $CR^6_2$ respectively wherein $R^6$ is alkyl or optionally substituted aryl or heteroaryl. Optional substituents for aryl or heteroaryl groups $R^6$ may be selected from $R^4$ or $R^5$.

In one preferred arrangement, R is $Ar^3$ and each of $Ar^1$, $Ar^2$ and $Ar^3$ are independently and optionally substituted with one or more $C_{1-20}$ alkyl groups.

Particularly preferred units satisfying Formula 1 include units of Formulae 1-3:

1

2

3 wherein $Ar^1$ and $Ar^2$ are as defined above; and $Ar^3$ is optionally substituted aryl or heteroaryl. Where present, preferred substituents for $Ar^3$ include substituents as described for $Ar^1$ and $Ar^2$, in particular alkyl and alkoxy groups.

Ar$^1$, Ar$^2$ and Ar$^3$ are preferably phenyl, each of which may independently be substituted with one or more substituents as described above.

In another preferred arrangement, aryl or heteroaryl groups of formula (V) are phenyl, each phenyl group being optionally substituted with one or more alkyl groups.

In another preferred arrangement, Ar$^1$, Ar$^2$ and Ar$^3$ are phenyl, each of which may be substituted with one or more C$_{1-20}$ alkyl groups, and r=1.

In another preferred arrangement, Ar$^1$ and Ar$^2$ are phenyl, each of which may be substituted with one or more C$_{1-20}$ alkyl groups, and R is 3,5-diphenylbenzene wherein each phenyl may be substituted with one or more alkyl groups.

(iii) Polymers comprising (hetero)arylene repeat units, either as homopolymers or with one or more co-repeat units such as (hetero)arylamine repeat units described above. Exemplary arylene repeat units include phenyl, fluorene and indenofluorene repeat units, each of which may optionally be substituted with one or more substituents such as alkyl or alkoxy groups.

Exemplary fluorene repeat units include repeat units of formula (IV):

(IV)

wherein R$^1$ and R$^2$ are independently H or a substituent and wherein R$^1$ and R$^2$ may be linked to form a ring.

R$^1$ and R$^2$ are optionally selected from the group consisting of hydrogen; optionally substituted Ar$^3$ or a linear or branched chain of Ar$^3$ groups, wherein Ar$^3$ is as described above; optionally substituted alkyl, for example C$_{1-20}$ alkyl, wherein one or more non-adjacent C atoms of the alkyl group may be replaced with O, S, substituted N, C=O and —COO—; and a crosslinking group as described above that may be either directly bound to the fluorene unit or spaced from the fluorene unit by a spacer group as described above. In the case where R$^1$ or R$^2$ comprises alkyl, optional substituents of the alkyl group include F, CN, nitro, and aryl or heteroaryl optionally substituted with one or more groups R$^4$ wherein R$^4$ is as described above.

In the case where R$^1$ or R$^2$ comprises aryl or heteroaryl, each aryl or heteroaryl group may independently be substituted. Preferred optional substituents for the aryl or heteroaryl groups include one or more substituents R$^3$.

Optional substituents for the fluorene unit, other than substituents R$^1$ and R$^2$, are preferably selected from the group consisting of alkyl wherein one or more non-adjacent C atoms may be replaced with O, S, substituted N, C=O and —COO—, optionally substituted aryl, optionally substituted heteroaryl, fluorine, cyano and nitro.

Where present, substituted N in repeat units of formula (IV) may independently in each occurrence be NR$^5$ or NR$^6$.

In one preferred arrangement, at least one of R$^1$ and R$^2$ comprises an optionally substituted C$_1$-C$_{20}$ alkyl or an optionally substituted aryl group, in particular phenyl substituted with one or more C$_{1-20}$ alkyl groups.

A host polymer comprising repeat units of formula (IV) may carry one or both of the unsaturated and ring-opening crosslinkable groups described above. Exemplary repeat units of formula (IV) carrying crosslinkable groups include the following, as described in WO 2005/049689:

(IVa)

(IVb)

Exemplary phenyl repeat units include repeat units of formula (V):

(I)

wherein R$^1$ is as described above; v is 0, 1, 2, 3 or 4; each R$^1$ is the same or different in the case where v is 2, 3 or 4; and adjacent groups R$^1$ may be linked to form a ring. Optionally, v is 1 or 2. Optionally, R$^1$ in each occurrence is an optionally substituted C$_1$-C$_{20}$ alkyl. Optionally, the unit of formula (I) is 1,4-linked.

In one preferred arrangement, the repeat unit of formula (I) is 1,4-linked and a substituent R$^1$ is present in the 2-position and optionally also in the 5-position.

The host polymer may comprise one, two or more of triazine repeat units, (hetero)arylamine repeat units and arylene repeat units as described above.

A host polymer comprising aromatic repeat units may form conjugated chains of aromatic units. This conjugation may be interrupted or reduced by inclusion of suitable repeat units in the polymer backbone, such as repeat units that form a twist in the polymer backbone and repeat units that break conjugation.

An example of a repeat unit that may cause a twist in the polymer backbone (for example by steric hindrance) is 1,4-phenylene substituted with one or more groups such as one or more alkyl or alkoxy groups, e.g. C$_{1-20}$ alkyl or alkoxy groups, in particular 2,5-disubstituted-1,4-phenylene repeat units.

A class of repeat units that may break conjugation include arylene or heteroarylene repeat units that are linked to adjacent repeat units through non-conjugating positions. Exemplary units of this kind include 1,2-phenylene repeat units and 1,3-phenylene repeat units, each of which may optionally be substituted with one or more substituents R$^1$ as described above, in particular or more alkyl or alkoxy groups, e.g. C$_{1-20}$ alkyl or alkoxy groups, and fluorene repeat units linked through 2- and/or 6-positions which again may optionally be substituted with one or more substituents such as one or more substituents $R^1$ as described above.

Another class of repeat units that may break conjugation include repeat units having formula —$Ar^6$—Sp-$Ar^6$— wherein each $Ar^6$ is an optionally substituted aryl or heteroaryl group and Sp is a spacer atom or chain comprising at least one non-conjugating atom between the two Ar groups. Exemplary $Ar^6$ groups include optionally substituted phenyl. Optional substituents may be one or more substituents $R^1$ as described above, in particular or more alkyl or alkoxy groups, e.g. $C_{1-20}$ alkyl or alkoxy groups. Exemplary groups Sp include groups of formula —$(CH_2)_m$— wherein m is at least 1, for example an integer between 1-10, and wherein each H may independently be replaced with a substituent, for example an alkyl group, and wherein one or more carbon atoms may be replaced with a heteroatom, for example O or S.

(iv) Non-conjugated polymers comprising pendant charge transporting groups. An example of such a polymer is polyvinylcarbazole (PVK).

Light-Emitting Dopants

Light-emitting dopants used in the crosslinked layer may be phosphorescent. If present, light-emitting dopants used in any other light-emitting layer of the device may be selected from fluorescent and phosphorescent dopants.

Phosphorescent light-emitting dopants include metal complexes comprising optionally substituted complexes of formula (II):

$$ML^1_qL^2_rL^3_s \qquad (II)$$

wherein M is a metal; each of $L^1$, $L^2$ and $L^3$ is a coordinating group; q is an integer; r and s are each independently 0 or an integer; and the sum of (a·q)+(b·r)+(c·s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Suitable coordinating groups for f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications.

The d-block metals are particularly suitable for emission from triplet excited states. These metals form organometallic complexes with carbon or nitrogen donors such as porphyrin or bidentate ligands of formula (III):

(III)

wherein $Ar^4$ and $Ar^5$ may be the same or different and are independently selected from optionally substituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon (for example, $Ar^4$ is optionally substituted and optionally fused phenyl) and $Y^1$ is nitrogen (for example, $Ar^5$ is optionally substituted and optionally fused pyridine) are particularly preferred.

Examples of bidentate ligands are illustrated below:

Each of $Ar^4$ and $Ar^5$ may carry one or more substituents. Two or more of these substituents may be linked to form a ring, for example an aromatic ring. Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example as disclosed in JP 2002-324679; carbazole which may be used to assist hole transport to the complex when used as an emissive material, for example as disclosed in WO 02/81448; bromine, chlorine or iodine which can serve to functionalise the ligand for attachment of further groups, for example as disclosed in WO 02/68435 and EP 1245659; and dendrons which may be used to obtain or enhance solution processability of the metal complex, for example as disclosed in WO 02/6655.

A light-emitting dendrimer typically comprises a light-emitting core bound to one or more dendrons, wherein each dendron comprises a branching point and two or more dendritic branches. Preferably, the dendron is at least partially conjugated, and at least one of the core and dendritic branches comprises an aryl or heteroaryl group.

Other ligands suitable for use with d-block elements include diketonates, in particular acetylacetonate (acac); triarylphosphines and pyridine, each of which may be substituted.

The one or more dopants used in the OLED may emit light of any colour within the visible spectrum.

A blue emitting dopant may optionally have a photoluminescent spectrum with a peak in the range of 400-480 nm. An example of a blue dopant is the phosphorescent dopant fac-tris(1-methyl-5-phenyl-3-propyl-[1,2,4]triazolyl) iridium(III) disclosed in WO 2004/101707

A green emitting dopant may optionally have a photoluminescent spectrum with a peak in the range of 490-560 nm. An example of a green dopant is the phosphorescent dopant fac-tris(2-phenylpyridine)iridium(III).

A red emitting dopant may optionally have a peak in its photoluminescent emission spectrum at around 570-630 nm.

An exemplary red emitter is fac-tris(1-phenylisoquinoline)iridium(III).

The dopant may be provided in an amount relative to the host material or materials of up to 10 mol %, up to 5 mol %, up to 2.5 mol %, up to than 2 mol %, up to 1 mol %, up to 0.5 mol % or up to 0.25 mol %.

The host and the light-emitting dopant may be physically mixed. Alternatively, the light-emitting dopant may be chemically bound to the host. In the case of a polymer host, the light-emitting dopant may be chemically bound as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

This binding may result in more efficient transfer of excitons from the host polymer to the light emitting dopant because it may provide intramolecular exciton transfer pathways unavailable to a corresponding mixed system.

Moreover, binding may be beneficial for processing reasons. For example, if the light emitting dopant has low solubility then binding it to a soluble host, in particular a soluble polymer, allows the light emitting dopant to be carried in solution by the host, enabling device fabrication using solution processing techniques. Furthermore, binding the light emitting dopant to the host may prevent phase separation effects in solution-processed devices that may be detrimental to device performance.

Charge Transporting and Charge Blocking Layers

A hole transporting layer may be provided between the anode and the light-emitting layer or layers. Likewise, an electron transporting layer may be provided between the cathode and the light-emitting layer or layers.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

If present, a hole transporting layer located between the anode and the light-emitting layers preferably has a HOMO level of less than or equal to 5.5 eV, more preferably around 4.8-5.5 eV. The HOMO level of the hole transport layer may be selected so as to be within 0.2 eV, optionally within 0.1 eV, of an adjacent layer (such as a light-emitting layer) in order to provide a small bather to hole transport between these layers.

If present, an electron transporting layer located between the light-emitting layers and cathode preferably has a LUMO level of around 3-3.5 eV. For example, a layer of a silicon monoxide or silicon dioxide or other thin dielectric layer having thickness in the range of 0.2-2 nm may be provided between the light-emitting layer nearest the cathode and the cathode. HOMO and LUMO levels may be measured using cyclic voltammetry.

A hole transporting layer may contain a hole-transporting (hetero)arylamine, such as a homopolymer or copolymer comprising hole transporting repeat units of formula (V). Exemplary copolymers comprise repeat units of formula (V) and optionally substituted (hetero)arylene co-repeat units, such as phenyl, fluorene or indenofluorene repeat units as described above, wherein each of said (hetero)arylene repeat units may optionally be substituted with one or more substituents such as alkyl or alkoxy groups. Specific co-repeat units include fluorene repeat units of formula (IV) and optionally substituted phenylene repeat units of formula (I) as described above.

An electron transporting layer may contain a polymer comprising a chain of optionally substituted arylene repeat units, such as a chain of fluorene repeat units.

The hole-transporting layer may be crosslinkable, in particular if it is formed by depositing a hole transporting material from a solution in a solvent. For example a polymer comprising a repeat unit of formula (V), optionally with one or more arylene co-repeat units, may be provided with crosslinkable substituents on one or more of the arylene repeat units and/or repeat units of formula (V).

Exciton Blocking Layer

An exciton blocking layer may be provided adjacent to a light-emitting layer in order to prevent excitons from migrating out of the light-emitting layer, which may result in quenching of the exciton or absorption and re-emission of the exciton at a longer wavelength. The exciton blocking layer may have a singlet and/or triplet excited state energy level that is higher than that of excitons generated in the light-emitting layer.

Hole Injection Layers

A conductive hole injection layer, which may be formed from a conductive organic or inorganic material, may be provided between the anode and the light-emitting layer or layers to assist hole injection from the anode into the layer or layers of semiconducting polymer. A hole transporting layer may be used in combination with a hole injection layer.

Examples of doped organic hole injection materials include optionally substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Cathode

The cathode is selected from materials that have a workfunction allowing injection of electrons into the light-emitting layer or layers. Other factors influence the selection of the cathode such as the possibility of adverse interactions between the cathode and the light-emitting materials. The cathode may consist of a single material such as a layer of aluminium. Alternatively, it may comprise a plurality of metals, for example a bilayer of a low workfunction material and a high workfunction material such as calcium and aluminium as disclosed in WO 98/10621. The cathode may contain a layer containing elemental barium, for example as disclosed in WO 98/57381, Appl. Phys. Lett. 2002, 81(4), 634 and WO 02/84759. The cathode may contain a thin layer of metal compound between the light-emitting layer(s) of the OLED and one or more conductive layers of the cathode, such as one or more metal layers. Exemplary metal compounds include an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977. The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate 1 preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

Suitable solvents for forming solution processable formulations of the composition may be selected from common organic solvents, such as mono- or poly-alkylbenzenes such as toluene and xylene.

Exemplary solution deposition techniques including printing and coating techniques such spin-coating, dip-coating, roll-to-roll coating or roll-to-roll printing, doctor blade coating, slot die coating, gravure printing, screen printing and inkjet printing.

Coating methods, such as those described above, are particularly suitable for devices wherein patterning of the light-emitting layer or layers is unnecessary—for example for lighting applications or simple monochrome segmented displays.

Printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Polymer Synthesis

Preferred methods for preparation of conjugated polymers, such as polymers comprising repeat units of formula (IV) and/or (V) as described above, comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable π-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular copolymers may be prepared when both reactive groups of a first monomer are boron and both reactive groups of a second monomer are halogen.

As alternatives to halides, other leaving groups capable of participating in metal insertion include sulfonic acids and sulfonic acid esters such as tosylate, mesylate and triflate.

White OLEDs

The OLED may contain a plurality of light-emitting layers, preferably two or 3 light-emitting layers, arranged such that emission from these layers is observed as white light.

Exemplary arrangements of light-emitting layers include the following:

Yellow light-emitting layer/Blue light-emitting layer
Green light-emitting layer/Red light-emitting layer/Blue light-emitting layer
Green+red light-emitting layer/Blue light-emitting layer
Green light-emitting layer/Blue+red light-emitting layer Spacer layers may be provided between any of these light-emitting layers, for example to prevent quenching of emission of one layer by the adjacent layer.

The white light may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-4500K.

The yellow, red, green and blue light-emitting materials for these devices may be selected from fluorescent or phosphorescent light-emitting materials known to the skilled person, as described above. One of these light-emitting layers is crosslinked using an unsaturated crosslinker and a ring-opening crosslinker as described above. The other light-emitting layer or layers may or may not be crosslinked using one or more crosslinkers described above.

The white OLED may include only phosphorescent light-emitting materials or a combination of fluorescent and phosphorescent light-emitting materials.

An exemplary blue fluorescent material of a blue light-emitting layer is a polymer comprising arylamine repeat units (V) as described above. This polymer may be a homopolymer or a copolymer, for example a copolymer with one or more arylene repeat units, for example fluorene repeat units (IV) or phenylene repeat units (I).

Applications

OLEDs as described herein may be used in a wide range of applications, including but not limited to use as display backlights, for example as displays or as white light sources for applications such as LCD backlights or area illumination. White light-emitting OLEDs as light sources may comprise uniform (unpatterned) emissive layers. OLEDs for use in displays may comprise a patterned emissive layer or layers and/or a patterned electrode to provide individual display pixels.

EXAMPLES

Polymer Example 1

Polymer Example 1 was formed by Suzuki polymerisation of a polymerisation mixture comprising the molar percentages of monomers illustrated below. The polymerisation was carried out as described in WO 00/53656.

50 mol%

6.8 mol%

10 mol%

20 mol%

3.2 mol%

Benzocyclobutane cross-linker
5 mol%

-continued

Double-bond cross-linker
5 mol%

Comparative Polymer 1

For the purpose of comparison, a polymer was prepared as described in Polymer Example 1, except that 10 mol % of the benzocyclobutane crosslinker was used, and no double-bond crosslinker was used.

Example 1

An organic light-emitting device having the following structure was formed on a glass substrate:
ITO/HIL/HTL/EL/Cathode
wherein ITO is an indium-tin oxide anode; HIL is a layer of hole-injection material available from Plextronics Inc.; HTL is a hole transport layer comprising a copolymer formed by Suzuki polymerisation of monomers described below; EL is a green phosphorescent light-emitting layer formed from Polymer Example 1; and Cathode is a cathode comprising a bilayer of a metal fluoride and aluminium.

HIL, HTL and EL were each formed by spin-coating a solution comprising the components of that layer and a solvent, and evaporating the solvent.

The copolymer forming HTL was formed by Suzuki polymerisation of the following monomers:

50 mol%

42.5 mol%

7.5 mol%

The hole-transporting polymer was crosslinked following its deposition to prevent dissolution of HTL upon deposition of the materials used to form the EL layer.

Following deposition of the composition for forming the EL layer, the composition was crosslinked by baking.

Comparative Device 1

For the purpose of comparison, a device was formed as described in Example 1 except that the EL layer was not cross-linked following deposition of the host-dopant composition.

Comparative Device 2

For the purpose of comparison, a device was formed as described in Example 1 except that Comparative Polymer 1 was used in place of Polymer Example 1

Comparative Device 3

For the purpose of comparison, a device was formed as described in Comparative Device 2 except that the EL layer was not cross-linked following deposition of the host-dopant composition.

Figure 2:
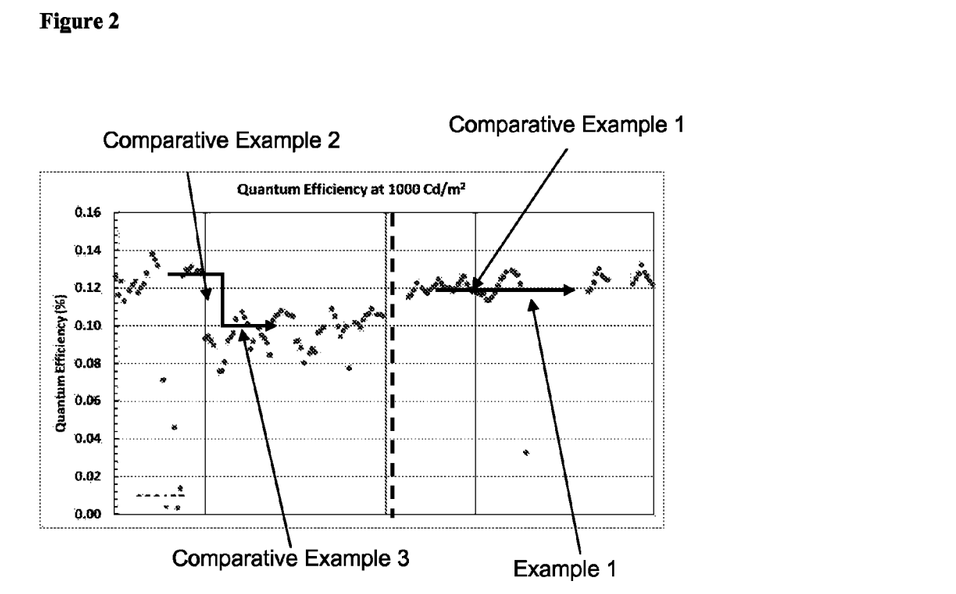
FIG. 2 illustrates quantum efficiency for a device according to the invention and comparative devices.

With reference to FIG. 2, it can be seen by comparing Comparative Device 1 (no crosslinking of the EL layer) and Example 1 (crosslinked EL layer) that their is no measured change in external quantum efficiency when the EL layer is crosslinked.

Again with reference to FIG. 2, it can be seen by comparing Comparative Devices 2 and 3 that crosslinking of an EL layer comprising benzocyclobutane crosslinkable groups only does result in a significant drop in external quantum efficiency.

Polymer Example 2

Polymer Example 2 was formed by Suzuki polymerisation of a polymerisation mixture comprising the molar percentages of monomers illustrated below. The polymerisation was carried out as described in WO 00/53656.

The polymer had a viscosity average weight, Mz, of 1,840,000, a weight average molecular weight, Mw, of 799,000, a peak average molecular weight, Mp, of 432,000 and a number average molecular weight Mn of 157,000. The polymer had a polydispersity of 5.09.

50 mol %

23.82 mol %

11.5 mol %

5 mol %

5 mol %

4.68 mol %

Comparative Polymer 2

Comparative Polymer 2 was formed by Suzuki polymerisation of a polymerisation mixture comprising the molar percentages of monomers illustrated below in which the 5 mol % of a monomer with a crosslinkable double bond group and the 5 mol % of a monomer with a crosslinkable benzocyclobutane group is replaced with 10 mol % of a monomer with a crosslinkable benzocyclobutane group. The polymerisation was carried out as described in WO 00/53656.

The polymer had a viscosity average weight, Mz, of 913,000, a weight average molecular weight, Mw, of 466,000, a peak average molecular weight, Mp, of 365,000 and a number average molecular weight Mn of 131,000. The polymer had a polydispersity of 3.58.

50 mol%

23.82 mol%

Comparative Device 4

A device was prepared as described for Device Example 2 except that Polymer Example 2 was annealed at 130° C. which resulted in substantially no crosslinking.

Comparative Device 5

A device was prepared as described for Device Example 2 except that Comparative Polymer 2 was deposited and crosslinked by heating to 180° C. to form the light-emitting layer in place of Polymer Example 2.

Comparative Device 6

A device was prepared as described for Comparative Device 5 except that Comparative Polymer 2 was annealed at 130° C. which resulted in substantially no crosslinking. With reference to Table 1, it can be seen that CIE x and y coordinates of Comparative Devices 4-6 and Device Example 2 are similar, but the fall in external quantum efficiency upon crosslinking is much greater for Comparative Device 5 than for Device Example 2.

Device Example 2

A device was prepared as described for Device Example 1 except that Polymer Example 2 was deposited in place of Polymer Example 1 and crosslinked by heating at 180° C. for 60 minutes to form a 75 nm thick light-emitting layer, and the hole-transporting layer was formed by spin-coating Hole Transporting Polymer 2, described below.

The hole injection layer was formed to a thickness of 50 nm and heated at 170° C. for 15 minutes. The hole-transporting layer was formed to a thickness of 22 nm and heated at 180° C. for 60 minutes.

Hole Transporting Polymer 2 was formed by Suzuki polymerisation of the following monomers as described in WO 00/53656:

|  | Comparative Device 4 (Polymer Example 2, no crosslinking) | Device Example 2 (Polymer Example 2, crosslinked) | Comparative Device 6 (Comparative Polymer 2, no crosslinking) | Comparative Device 5 (Comparative Polymer 2, crosslinking) |
|---|---|---|---|---|
| Colour (CIEx) | 0.282 | 0.281 | 0.279 | 0.281 |
| Colour (CIEy) | 0.653 | 0.653 | 0.651 | 0.647 |
| EQE (%) | 11.87 | 11.38 | 9.75 | 8.45 |
| % drop on cross-linking |  | 4.20% |  | 13.30% |

Without wishing to be bound by any theory, it is believed that crosslinking between two ring systems such as benzocyclobutane results in formation of a species with a low excited state energy level that causes quenching of luminescence of any dopant having a higher energy than that species (in this case, the triplet energy level of the green phosphorescent dopant).

Again without wishing to be bound by any theory, it is believed that use of a combination of a crosslinker comprising an unsaturated carbon-carbon bond group and a crosslinker comprising a ring system capable of undergoing ring-opening crosslinking may result in crosslinking between the unsaturated carbon-carbon bond group and the ring system in preference to crosslinking between the two ring systems, thereby preventing formation of the aforementioned species with a low excited state energy level.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A crosslinkable light-emitting composition comprising at least one host material, at least one phosphorescent light-emitting dopant, a first crosslinker comprising an unsaturated carbon-carbon bond group and a second crosslinker comprising a ring system capable of undergoing ring-opening crosslinking, wherein the first crosslinker and the second crosslinker are repeat units of a crosslinkable polymer and wherein the crosslinkable polymer is the only crosslinkable polymer of the composition.

2. A crosslinkable light-emitting composition according to claim 1 wherein the at least one phosphorescent light-emitting dopant is blended with the at least one host material.

3. A crosslinkable light-emitting composition according to claim 1 wherein the at least one phosphorescent light-emitting dopant is bound to the at least one host material.

4. A crosslinkable light-emitting composition according to claim 1 wherein the first crosslinker comprises a carbon-carbon double bond.

5. A crosslinkable light-emitting composition according to claim 1 wherein the ring system comprises cyclobutane.

6. A crosslinkable light-emitting composition according to claim 1 wherein the ring system comprises an optionally substituted polycyclic ring system.

7. A crosslinkable light-emitting composition according to claim 6 wherein the polycyclic ring system comprises an optionally substituted benzocyclobutane group.

8. A crosslinkable light-emitting composition according to claim 1 wherein the at least one host material is a polymer.

9. A crosslinkable light-emitting composition according to claim 8 wherein the phosphorescent light-emitting dopant is a repeat unit in the host material polymer main chain, a side group of the host material polymer or an end-group of the host material polymer.

10. A crosslinkable light-emitting composition according to claim 1 wherein the second crosslinker is capable of forming a diene, the diene being capable of reacting with the unsaturated carbon-carbon bond group of the first crosslinker.

11. A formulation comprising a crosslinkable light-emitting composition according to claim 1 and at least one solvent.

12. A method of forming an organic light-emitting device comprising the steps of:
    forming a first organic light-emitting layer by depositing a crosslinkable light-emitting composition according to claim 1 over a first electrode for injection of charge carriers of a first type and crosslinking the crosslinkable groups; and
    forming a second electrode for injection of charge carriers of a second type over the first organic light-emitting layer.

13. A method according to claim 12 wherein the crosslinkable light-emitting composition further comprises at least one solvent.

14. A method according to claim 12 wherein an organic layer is deposited onto the first organic light-emitting layer from a solution in a solvent.

15. A method according to claim 14 wherein the organic layer is selected from a second light-emitting layer; a charge transporting layer; a charge blocking layer; and an exciton blocking layer.

16. An organic light-emitting device comprising a crosslinked light-emitting layer formed from a crosslinkable light-emitting composition according to claim 1.

17. An organic light-emitting device according to claim 16 which is a white organic light-emitting device.

18. An organic light-emitting device according to claim 16 comprising at least one further light-emitting layer in addition to the crosslinked light-emitting layer.

19. A crosslinkable light-emitting composition according to claim 4 wherein the carbon-carbon double bond is a terminal double bond.

* * * * *